(12) United States Patent
Ye et al.

(10) Patent No.: US 10,517,466 B2
(45) Date of Patent: Dec. 31, 2019

(54) CAPSULE ENDOSCOPE HAVING A SELF-CLEANING SURFACE AND METHOD OF USING THE SAME

(71) Applicants: Qing Ye, Los Gatos, CA (US); Xiaodong Duan, Plansaton, CA (US)

(72) Inventors: Qing Ye, Los Gatos, CA (US); Xiaodong Duan, Plansaton, CA (US)

(73) Assignee: ANKON MEDICAL TECHNOLOGIES (SHANGHAI), LTD, Shanghai (CN)

( * ) Notice: Subject to any disclaimer, the term of this patent is extended or adjusted under 35 U.S.C. 154(b) by 633 days.

(21) Appl. No.: 14/673,882

(22) Filed: Mar. 31, 2015

(65) Prior Publication Data

US 2016/0287058 A1 Oct. 6, 2016

(51) Int. Cl.
| | |
|---|---|
| *A61B 1/00* | (2006.01) |
| *A61B 1/04* | (2006.01) |
| *A61B 1/12* | (2006.01) |
| *A61B 1/06* | (2006.01) |

(52) U.S. Cl.
CPC .......... *A61B 1/00158* (2013.01); *A61B 1/126* (2013.01); *A61B 1/041* (2013.01); *A61B 1/0661* (2013.01)

(58) Field of Classification Search
CPC ................................ A61B 1/041; A61B 1/126
See application file for complete search history.

(56) References Cited

U.S. PATENT DOCUMENTS

| | | | | |
|---|---|---|---|---|
| 5,324,566 A | * | 6/1994 | Ogawa | B05D 1/185 428/141 |
| 2012/0265015 A1 | * | 10/2012 | Kawano | A61B 1/00016 600/118 |
| 2015/0018614 A1 | * | 1/2015 | Duan | A61B 1/00149 600/109 |
| 2015/0289751 A1 | * | 10/2015 | Frerck | A61B 1/00135 600/121 |

FOREIGN PATENT DOCUMENTS

CN 103222842 A * 7/2013 ......... A61B 1/00149

* cited by examiner

*Primary Examiner* — Alexandra L Newton
(74) *Attorney, Agent, or Firm* — Treasure IP Group, LLC (57) ABSTRACT

The present invention discloses a capsule endoscope and a method to prevent the capsule from being covered by a residue or mucous in a patient's digestive tract. The capsule endoscope comprises an improved surface, preventing a residue or mucous to adhere onto the surface of the capsule, and in the unlikely event that a residue or a mucous is collected by the capsule the improved surface can allow an easy and successful clean before an image is taken.

6 Claims, 11 Drawing Sheets

CAPSULE ENDOSCOPE HAVING A SELF-CLEANING SURFACE AND METHOD OF USING THE SAME

CROSS REFERENCE TO RELATED APPLICATIONS

This application is a provisional application.

TECHNICAL FIELD

The invention relates to medical apparatus and instruments, specifically refers to a capsule endoscope having a surface modification for self-cleaning.

BACKGROUND OF THE INVENTION

Capsule endoscope is a miniaturized camera placed inside a capsule-shaped housing. When a patient swallows such a camera pill, the capsule endoscope travels along the patient's gastrointestinal tract and takes a series of pictures of the interior of the patient gastrointestinal tract. While the capsule endoscope passing through the patient's digestive system, the images taken would be simultaneously transmitted outside of the patient's body to a receiver, and then doctors use the image data for real-time medical examinations.

Capsule endoscopy not only has shown clear advantage in examining a patient's small intestine, where the areas or portions of the gastrointestinal tract are not readily accessible by traditional standard endoscopy techniques, but also demonstrate significant usefulness in examining regular organs like-stomach.

However, when examining a stomach, in order to fully examine an interior surface of the stomach, it normally requires a patient to empty the stomach first and drink a lot of water to expand the interior surface of a stomach. At the same time, water makes the residues in the stomach travel from one position to another. As a capsule navigate through stomach and adjust its pastures in the liquid or on the surface of the stomach, often in times, the capsule gather a residue on its end. If accidentally, the residue landed on the surface of an imaging device or a lighting unit is accidentally covered, then the images generated by capsule endoscope will not have much useful information.

Therefore there is need to either prevent the capsule to be covered by the residues or to easily remove the residue off from the surface of capsule without taking the capsule out from the interior of the stomach.

SUMMARY OF THE INVENTION

The present invention discloses a capsule endoscope and a method to prevent the capsule from being covered by a residue or mucous in a patient's digestive tract. The capsule endoscope comprises an improved surface, which offers self clean. The improved surface prevents a residue or mucous to adhere onto the surface of the capsule, and in the unlikely event that a residue or a mucous is collected by the capsule because capsule has to pass through a narrow channel, the improved surface can allow an easy and successful clean before an image is taken.

It is one object of the present invention that to provide a self-clean surface for a capsule endoscope while the self-clean surface does not interfere with the light propagation pathway of the imaging device thereof.

It is another object of the present invention that to provide a self-clean surface for a capsule endoscope while the self-clean surface does not interfere with the light propagation pathway of the emitter or the illumination device thereof.

It is another object of the present invention that to provide a self-clean surface for a capsule endoscope while the self-clean surface comprises a coating, wherein the coating is strongly adhered to the surface of the capsule and does not release a small molecular residue by chain scission if the surface of the capsule endoscope is rubbing the walls of an interior surface by friction.

It is another object of the present invention that to provide a self-clean surface for a capsule endoscope while the self-clean surface comprises a coating, wherein the coating is chemically bond to the surface of the capsule and substantially chemical inert, which does not release any small molecular residue to the surrounding liquid environment through any chemical reaction.

In one aspect of the present invention, the capsule endoscope described herein. The capsule endoscope comprises a capsule endoscope in a target environment and an external magnetic assembly. The capsule endoscope comprises a housing having a first surface and a second surface, wherein the first and second surfaces comprise a first and second self-clean coatings; a permanent magnetic dipole, placed inside of the housing; an imaging device, displaced inside of the housing, underneath of the first surface of the housing, configured to examining an interior surface of the target area; and an emitter, placed inside of the housing, underneath of the second surface of the housing, configured to provide illumination for the imaging device.

The exterior magnetic assembly, configured to generate an external magnetic field in proximity to interact with the permanent magnetic dipole inside the capsule endoscope to change its location or orientation of the capsule endoscope.

In one embodiment of the present invention, the first self-clean coating comprises a fluorinated polymer.

In another embodiment of the present invention, the first self-clean coating comprises physical geometric patterns.

In another aspect of the present invention, a method to use a capsule endoscope having a self-clean surface when the capsule endoscope is placed in situ is described. The method comprises providing a capsule endoscope having a permanent magnetic dipole in situ in a target area having a liquid; changing the position or orientation of the capsule endoscope with respect to the liquid by moving an external magnet; cleaning a surface of the capsule endoscope by contacting the surface with the liquid; and examining the interior of the target area by using a imaging device in the capsule endoscope.

In one embodiment of the present invention, the step of cleaning a surface of the capsule endoscope by contacting the surface with the liquid comprises moving the end of the capsule endoscope having the imaging device above and blew the liquid/gas interface.

In another aspect of the present invention, the step of cleaning a surface of the capsule endoscope by contacting the surface with the liquid comprises proving a rotational magnetic field by the external magnet to rotate the capsule endoscope and change its tilt angle from −90 degrees to 90 degrees.

DETAILED DESCRIPTION OF THE PREFERRED EMBODIMENTS

Exemplary embodiments of a capsule endoscope according to the present invention are explained in detail below with reference to the accompanying drawings. The present invention is not limited to the embodiments.

Ingestible wireless medical capsules are known in the medical arts. Such wireless capsule is swallowed and travels through the digestive tract, collecting images and transmitting image data during the course of its journey, for medical examination. When a capsule endoscope is equipped with a permanent magnetic dipole, the capsule endoscope can be navigated to a target location and adopt a desired orientation.

The Capsule Endoscope Shape and Composition

Figure 1:
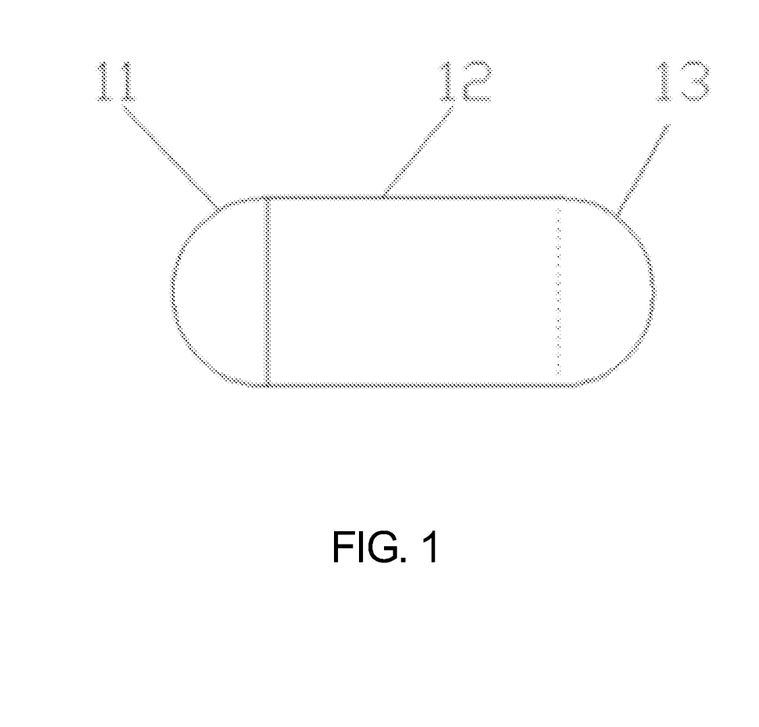
FIG. 1 is a schematic illustration of a capsule endoscope having a self-clean coating.

The capsule endoscope can be of any shape or in any size of a pill as in the general art. In one example, the capsule is cylindrical shaped with hemispherical ends. Or the capsule can have one end larger than the other end. Or an American football shaped capsule is to have two pointed ends. The capsule endoscope in the present invention is preferred to be symmetrical along its length direction. The capsule endoscope in the present invention has a housing. As shown in FIG. 1, in the capsule endoscope, the housing is preferred to be cylindrical shaped having two hemisphere ends (11 an 13). One end (13) is formed integrally with the cylindrical body (12) of the capsule housing and the other end (11) can become detachable from the rest of capsule housing. In one example, a first end 11 is the front end of the capsule endoscope and a second end 13 is the rear end of the capsule endoscope.

Figure 3:
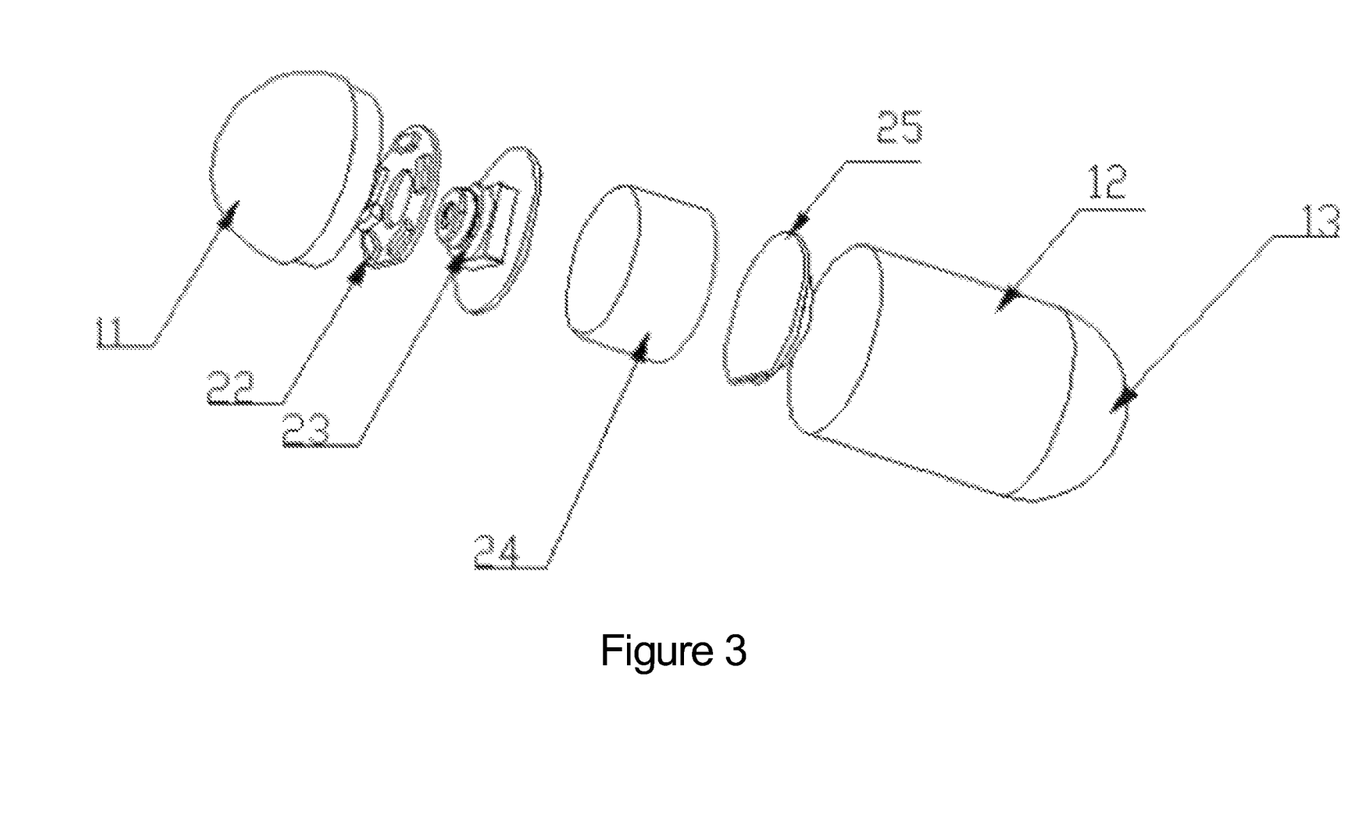
FIG. 3 is a schematic illustration of an exemplary capsule endoscope in accordance with the aspects of the present invention.

As shown in FIG. 3, the capsule endoscope further comprises an illumination device 22, imaging device 23, battery 24 and a RF transmission device 25, which are all enclosed in the housing of the capsule endoscope. In one example, the illumination device 22 and the imaging device 23 are placed at the same end of the capsule endoscope. In one instance, the imaging device 23 is placed at the front end 11 of the capsule endoscope. In a further instance, the illumination device 22 comprises five LEDs, which are evenly distributed around of the imaging device 23, wherein the imaging device 23 points to a center of the hemispherical end of the front end 11.

The capsule endoscope preferably further comprises a permanent magnetic dipole, which has a magnetization direction either parallel or perpendicular to the length of the cylindrical body 12 of the capsule endoscope. The permanent dipole in the capsule endoscope housing can interact with and move in response to an external magnet, which generates a 5-dimensional moving and rotational magnetic field, to determine a location and orientation of the capsule endoscope.

Self Clean Composition

The capsule endoscope provided herein, comprises a housing and a self-clean coating disposed on the exterior of the housing. The housing of the capsule endoscope comprises a first and second surface areas. In one example, the first surface area comprises a self-clean coating, which does not interfere with the light propagation pathway of the imaging device underneath the coating. In another example, a second surface area comprises a second self-clean coating, which does not interfere with the light propagation pathway of light propagation pathway of the emitter or the illumination device placed inside the housing underneath the second coating. In one preferred example, the first and second surface areas are located on the same end of the capsule endoscope. In still another preferred example, the first and second surface areas are located at the front end of the capsule endoscope. Wherein the first and second self-clean coating has the same composition.

In a first aspect, in one embodiment of the present invention, the first self-clean coating comprises a fluorinated polymer. The fluorinated polymer comprises $CF_3$—$(CF_2)_n$—$(CH_2)$-moiety, wherein n is an integer and greater than 1 and less than 20. In one example, the fluorinated polymer is formed on the first or second surface area by reacting a hetero-atom on the first and surface with a $CF_3$—$(CF_2)_n$—$(CH_2)$—$SiCl_3$. In another example, the fluorinated polymer is formed on the first or second surface area by depositing a layer of coating formulation comprising $CF_3$—$(CF_2)_n$—$(CH_2)$—R, R is any aliphatic group.

Figure 5:
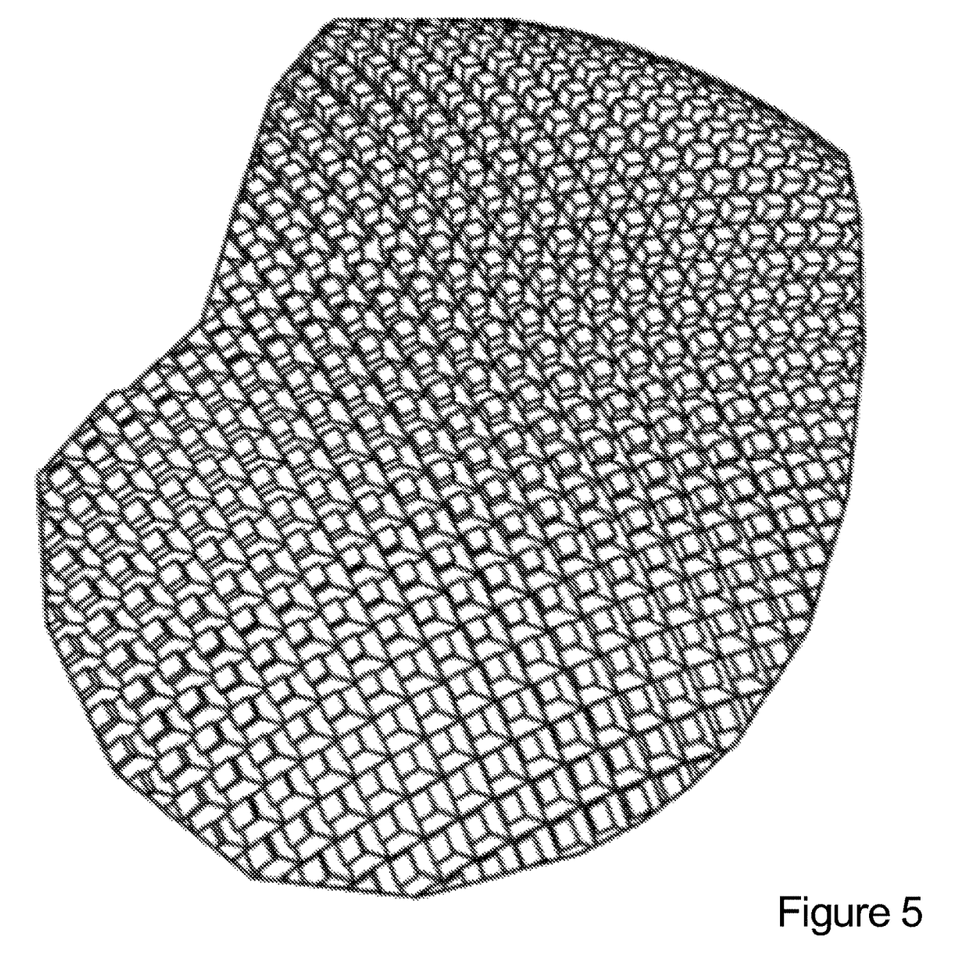
FIG. 5 is a schematic illustration of the surface geometric patterns for a capsule endoscope in accordance with the aspects of the present invention.
Figure 6:
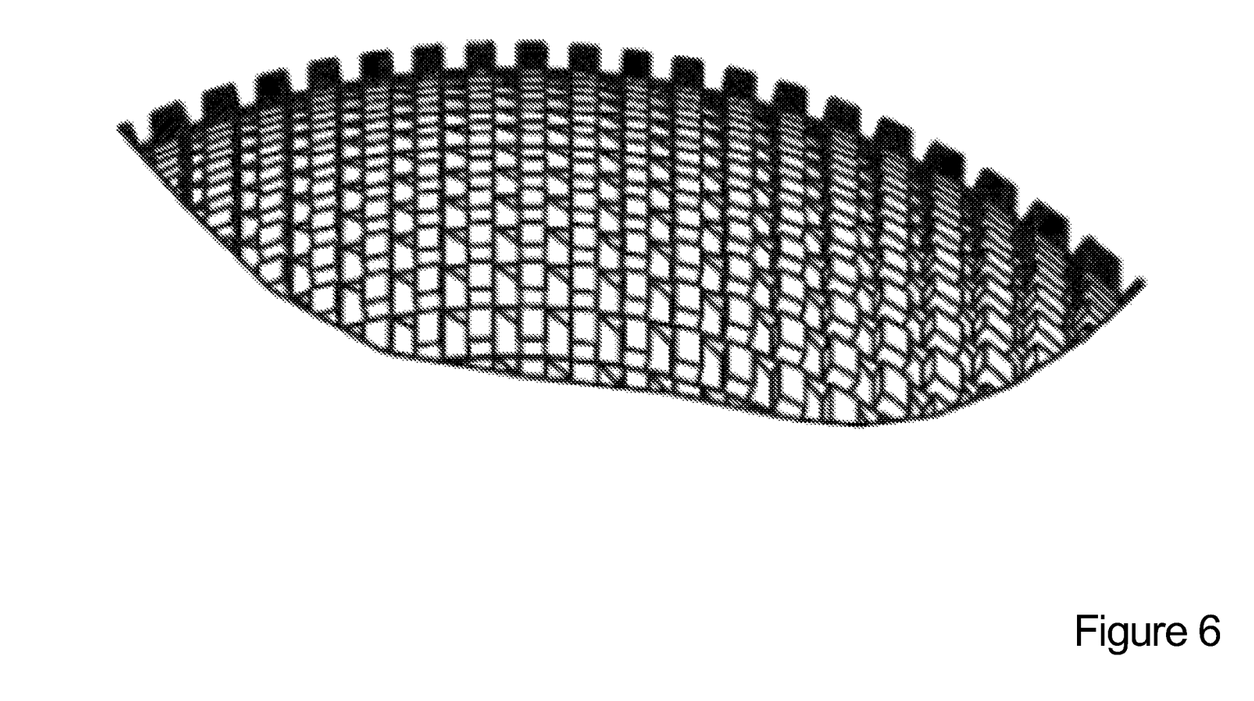
FIG. 6 is another schematic illustration of surface geometric patterns for a capsule endoscope in accordance with the aspects of the present invention.

In another embodiment of the present invention, the self-clean coating comprises physical geometric patterns. The physical geometric patterns are a plurality of periodical nanostructures, comprising peaks and valleys. FIGS. 5 and 6 are exemplary schematic illustrations of the physical geometry patterns in accordance with the aspects of the present invention.

In still another embodiment of the present invention, the self clean coating comprises a physical geometric patterns on the exterior of the housing which is further coated with a layer of chemical coating, for example fluorinated polymers.

In a second aspect, in one embodiment of the present invention, the self-clean coating for the first or second surface areas has a thickness less than 500 nm. In another example, the self-clean coating for first or second surface areas has a thickness less than 400 nm. In another example, the self-clean coating for first or second surface areas has a thickness less than 300 nm. In another example, the self-clean coating for first or second surface areas has a thickness less than 250 nm. In another example, the self-clean coating for first or second surface areas has a thickness less than 200 nm. In another example, the self-clean coating for first or second surface areas has a thickness less than 150 nm.

In a third aspect, the self-clean coating for the first or second surface areas is biological safe in in vivo conditions. In one embodiment the coating is strongly adhered to the surface of the capsule and does not release a small molecular residue by chain scission if the surface of the capsule endoscope is rubbing the interior walls of a digestive track.

In another embodiment, the self-clean coating is chemically bond to the surface of the capsule and substantially chemical inert, which does not release any small molecular residue to the surrounding liquid environment through any chemical reactions.

In a fourth aspect, the self-clean coating for the first or second surface areas further comprises an adhesion promoter, which helps the self-clean coating binds to the surface of the capsule housing. In one example, the adhesion promoter is a layer of $SiO_2$ directly formed on top of the housing of the capsule endoscope.

In a fifth aspect, the first and second surface areas bear the self-cleaning coating has low surface energy, characterized in that a water droplet can easily roll off from the surface rather than being spread. In one example, the first and second surface areas have a contact angle of 90° or more. In another example, the first and second surface areas have a contact angel of 100° or more. In another example, the first and second surface areas have a contact angel of 110° or more. In another example, the first and second surface areas have a contact angel of 120° or more. In another example, the first and second surface areas have a contact angel of 130° or more. In another example, the first and second surface areas have a contact angel of 140° or more. In another example, the first and second surface areas have a contact angel of 150° or more. In another example, the first and second surface areas have a contact angel of 165° or more. In another example, the first and second surface areas have a contact angel of 180° or less. In the scope of the present invention, the contact angle between a substance (eg. a liquid or residue or a mucous) on a curved surface of the capsule endoscope is reduced to the contact angle between the substance and the tanget plane at the contact point of the curved surface.

Further, the first and second surface having the self-clean coating form very low roll-off angles. In one example, the roll-off angles for the first and second surface is 50° or less. In another example, the roll-off angles for the first and second surface is 40° or less. In another example, the roll-off angles for the first and second surface is 30° or less. In another example, the roll-off angles for the first and second surface is 20° or less. In another example, the roll-off angles for the first and second surface is 10° or less. In another example, the roll-off angles for the first and second surface is 5° or less.

Optical Composition

Figure 2:
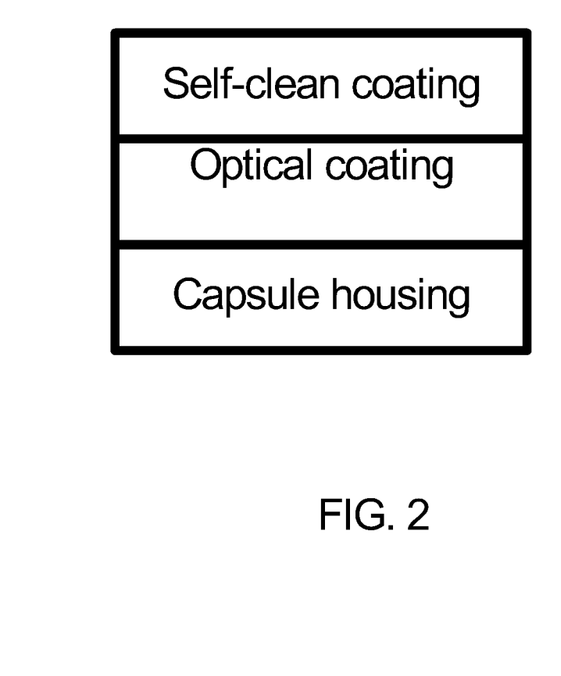
FIG. 2 is a schematic illustration of a surface modified capsule endoscope having a self-clean coating.

Further, referring to FIG. 2, the capsule endoscope disclosed herein, optionally, not only comprising a self-clean coating, but also an optical coating as well. The optical coating is sandwiched in between the surface of the housing and the self-clean coating.

In one embodiment, the optical coating is an out-coupling film gathering the light generated by the emitter inside the housing and being extracted/out-coupled to the outside of the housing. In another embodiment, the optical coating is an anti-reflection film, which prevents surface reflection and redirects the light into the capsule housing arriving at the camera or imaging device.

In one example, the optical coating comprises alternating layers of $SiO_2/TiO_2$. In one instance, alternating $TiO_2/SiO_2/TiO_2/SiO_2/TiO_2/SiO_2$ are deposited onto the surface of polycarbonate, with $TiO_2$ is in direct contact with $TiO_2$, and $SiO_2$ as the top layer, which is next to fluorinated silane.

Housing Material Composition

In accordance with the aspects of the present invention, the capsule endoscope has a housing. The housing is preferably made of a polymer which is chemically and biologically inert in a patient's digestive track and mechanically durable through the digestive track. In one example, the housing is made of polycarbonate. In another example, the housing is made of PSF.

Target Location (Liquid, Liquid/Gas Interface)

The capsule endoscope described herein, having a self-clean surface, is intended to be placed in a target area of an internal organ. The capsule is navigated to the target area by an external magnet and examining an interior wall of the target area while it is suspended. In one example, the target area is a stomach and the stomach is partially filed with a liquid having a liquid/gas interface, and at least sometimes the capsule endoscope is suspended at the liquid/gas interface. In another example, the target area is a small intestine and the small intestine is filed with a liquid, and at least sometimes the capsule endoscope is fully immersed in the liquid. In another example, the target area is a colon and the colon is filed with a liquid, and at least sometimes the capsule endoscope is fully surrounded by the liquid.

In accordance with another aspect of the present invention, a method of using a capsule endoscope having a self-clean surface is described. The method to provide a capsule endoscope having a self-clean surface when it is placed in vivo, comprises a) providing a capsule endoscope having a permanent magnetic dipole in situ in a target area having a liquid;

b) changing the position or orientation of the capsule endoscope with respect to the liquid by moving an external magnet;

c) cleaning a surface of the capsule endoscope; and d) examining the interior of the target area by using a imaging device in the capsule endoscope.

Figure 7:
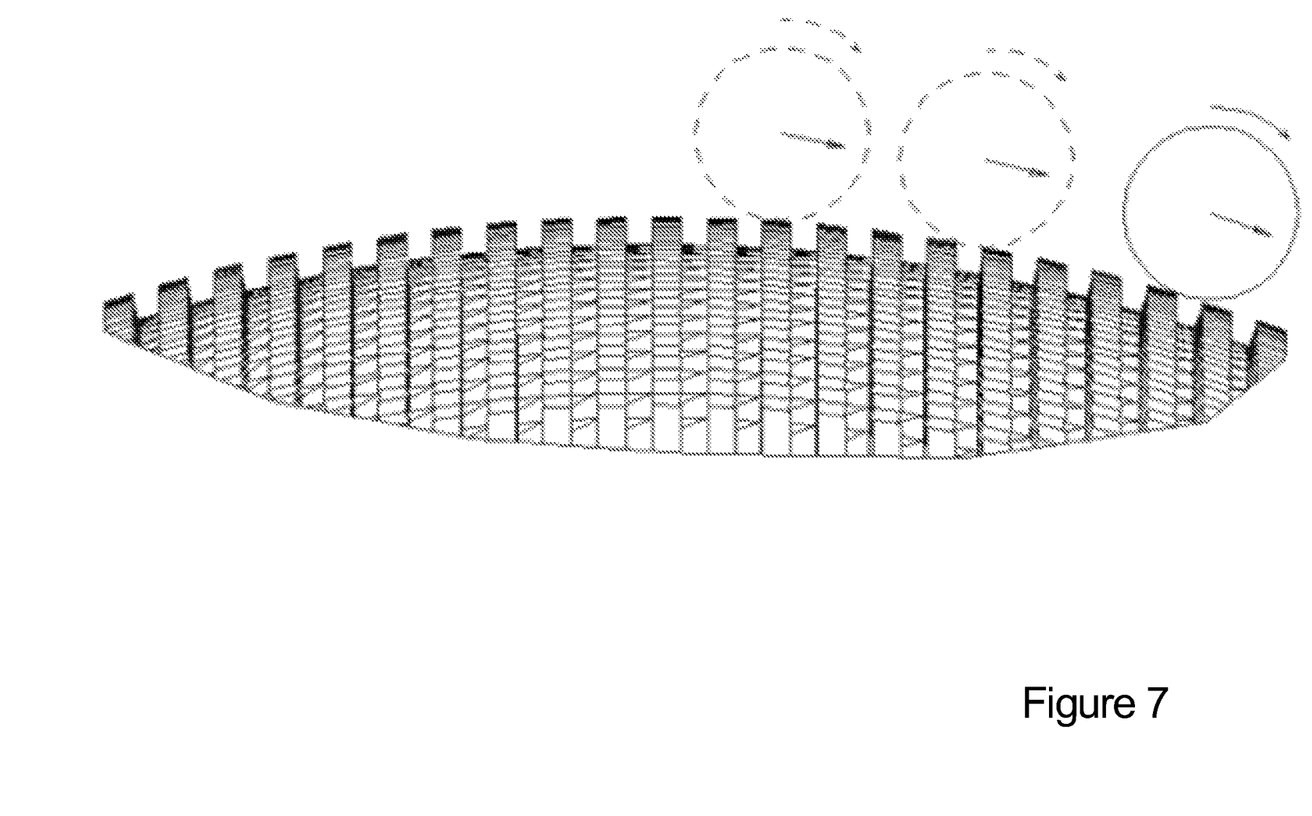
FIG. 7 is a detail schematic illustration to shown how the surface is cleaned in accordance with the aspects of the present invention.

When the capsule endoscope is introduced into the stomach to examine the interior wall thereof, the capsule is suspended at the gas and liquid interface forming a tilt angle of θ. Because the first end bearing the image device is exposed above the liquid/gas interface, in one instance, condensation can form on the first end obstructing the view of the imaging device. In this case, the capsule endoscope can slightly change the tilt angle of θ to have the condensed droplets roll off from the surface, as shown in FIG. 7.

In one embodiment, the cleaning step in the method further comprises suspending the capsule endoscope in a liquid/gas interface in the target area, wherein the capsule endoscope and the liquid/gas interface form an tilt angle θ; and changing the tile angle θ to make the condensed droplets fall off from the surface of the first end of the capsule endoscope.

Figure 8:
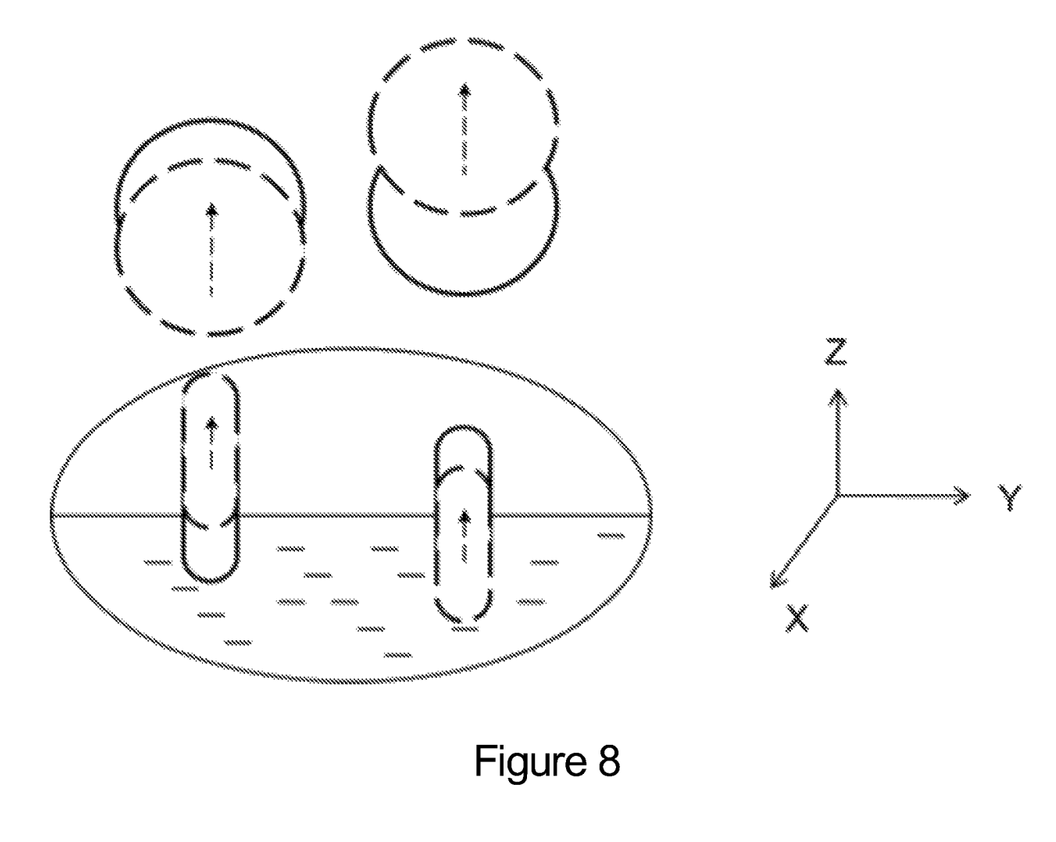
FIG. 8 is a schematic illustration to shown in one embodiment, the external magnet is moved vertically in order to move the capsule up and down to clean its surface, in accordance with the aspects of the present invention.
Figure 9:
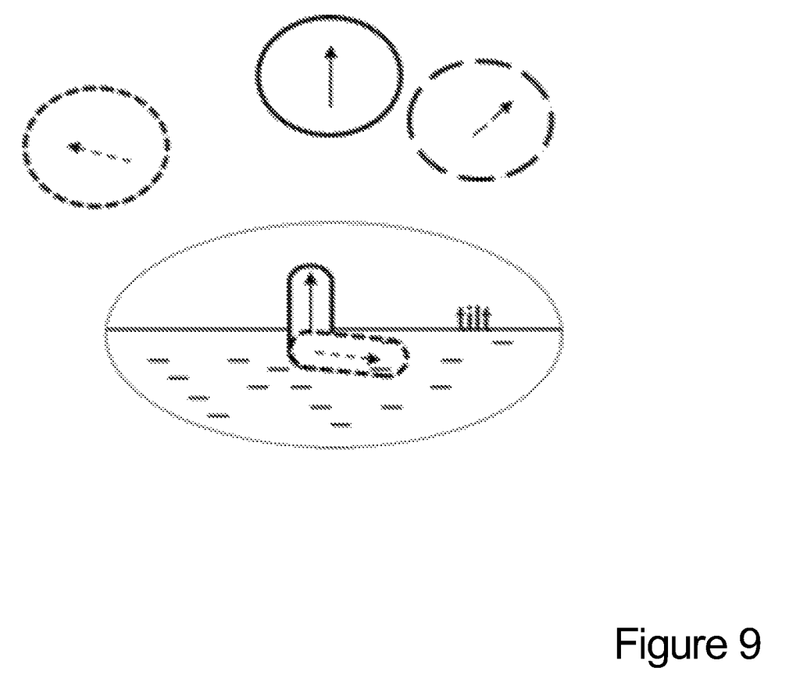
FIG. 9 is a schematic illustration to shown in another embodiment, the external magnet is moved laterally and rotated in order to make the imaging end of the capsule rotate in and out of the liquid to clean the surface thereof, in accordance with the aspects of the present invention.
Figure 10:
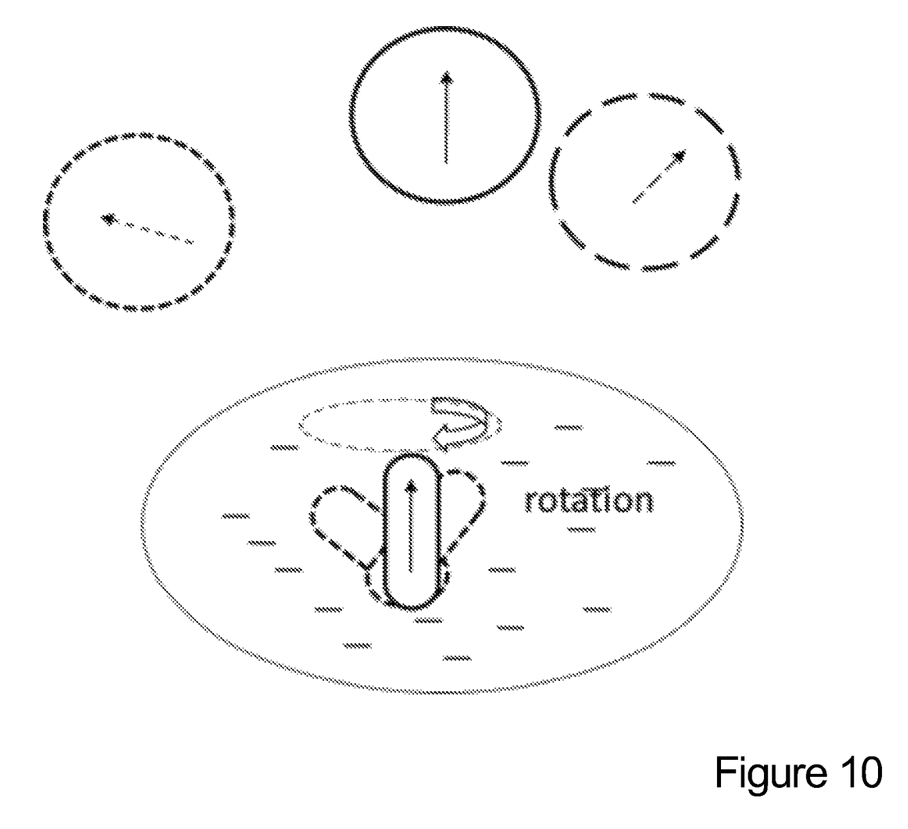
FIG. 10 is a schematic illustration to show in another embodiment, the external magnet is moved in five degree of freedom in order to make the imaging end of the capsule rotate in the liquid to clean the surface, in accordance with the aspects of the present invention.
Figure 11:
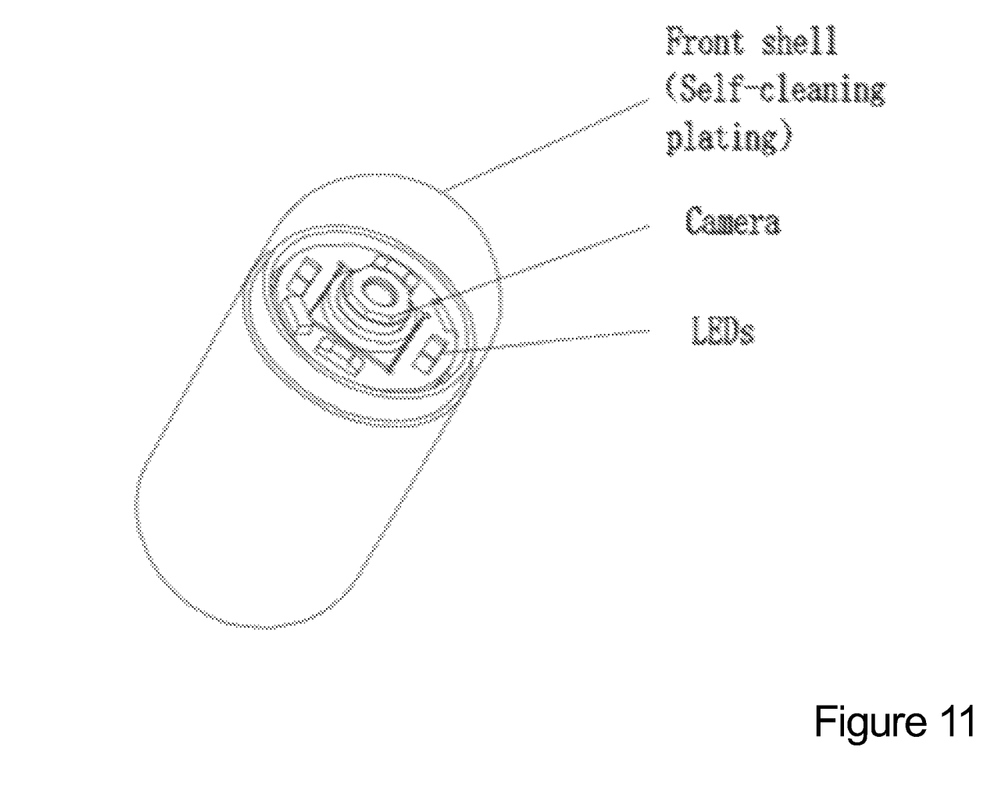
FIG. 11 is an illustration to show that an imaging device a camera and a light emitting device are placed under a housing having a self cleaning coating.
Figure 12:
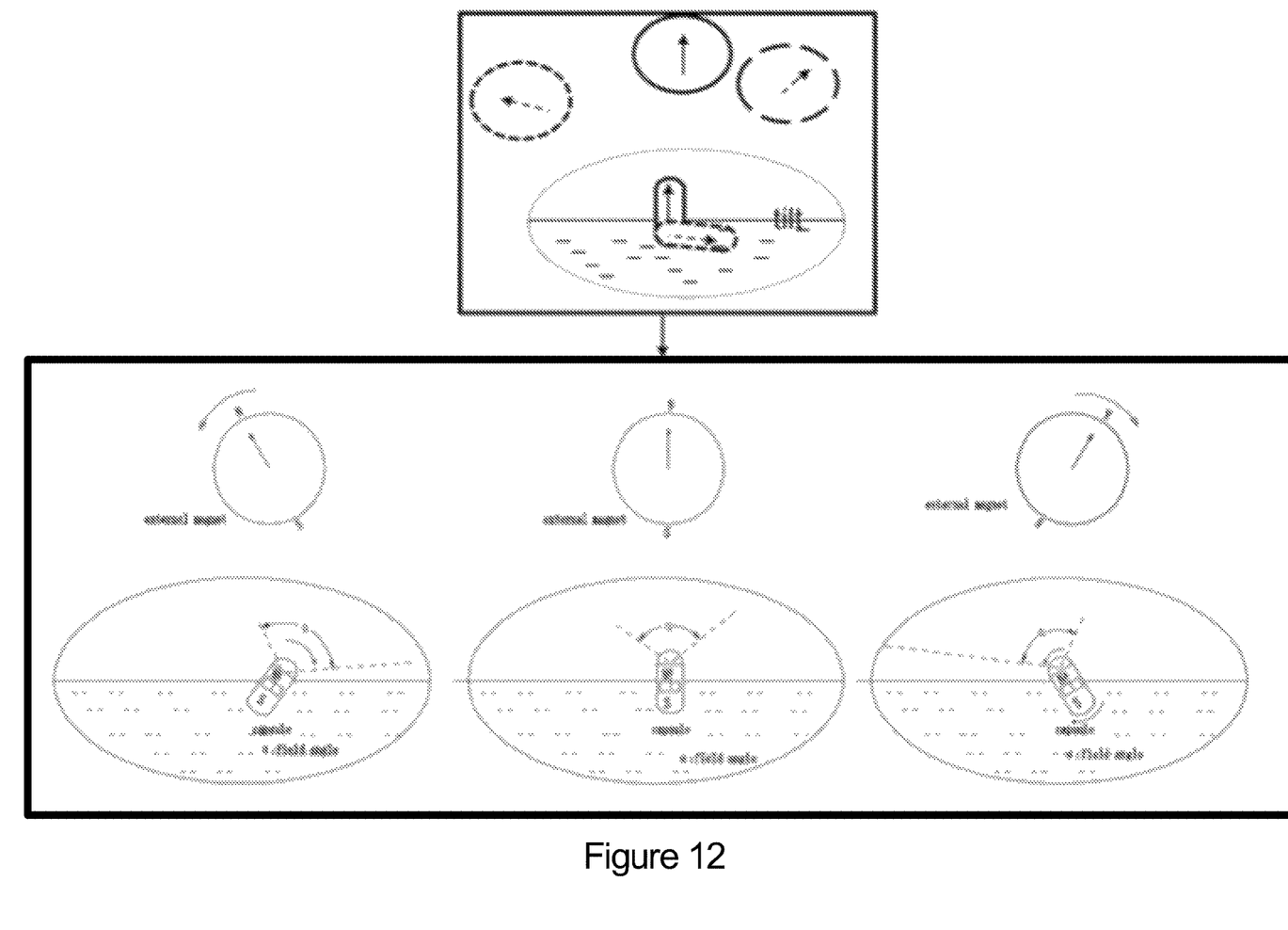
FIG. 12 is a schematic illustration to show that a cleaning step occurs before the examination step.

When the capsule is suspended at the gas and liquid interface forming a tilt angle of θ, in another example, the first end bearing the image device is exposed above the liquid/gas interface, in one example, the first end has a residue or mucous which does not fall off from the surface by changing the tilt angle θ or swirling around. Under this circumstance, in one instance, the capsule endoscope can be moved up and down vertically to let the first end of the capsule endoscope go above and under the liquid/gas interface to remove the reside or mucous on the first end as shown in FIG. 8. This step can be repeated for multiple times. In another instance, the capsule endoscope can be turned to the left or to the right to be immersed under the liquid, in other words, the capsule endoscope can rotate from −90 to 180 degrees in a plane perpendicular to the liquid/gas interface, to let the first end of the capsule endoscope go above and under the liquid/gas interface in order to remove the mucous (FIG. 9).

In one embodiment, the cleaning step in the above method further comprises moving the external magnet up and down to cover and uncover an end of the capsule endoscope having an imaging device by the liquid in the target area.

Alternatively, in another embodiment, the cleaning step in the method further comprises rotating the external magnet to provide a rotational magnetic field to rotate the capsule endoscope and change its tilt angle from −90 degrees to 180 degrees.

When the capsule endoscope is navigated into the small intestine and colon to examine the interior walls thereof, the capsule endoscope is surrounded by a liquid. The first end of the capsule endoscope bearing an image device may have collected residue or a mucous through its journey in the digestive track. Because the low surface energy provided by the self-clean coating in the present invention, the mucous or residue will have less affinity to the surface and being picked up by the surface in the first place. Further, in the event the residue or mucous is collected by the surface during the journey of capsule traveling in the digestive track, they can come off from the first end of the capsule endoscope by rubbing the surface of the first end with the interior walls in the presence or absence of a liquid. The action of rubbing can be triggered by the passive motion of the capsule due to the bowl movement, for both mechanically controllable capsule endoscopes and the uncontrollable counterparts. Additionally, the rubbing action can also accomplished by actively rotate the mechanically controllable capsule endoscope if there is an enough space in the small bowl or colon.

EXPERIMENTAL

Example 1

Figure 4:
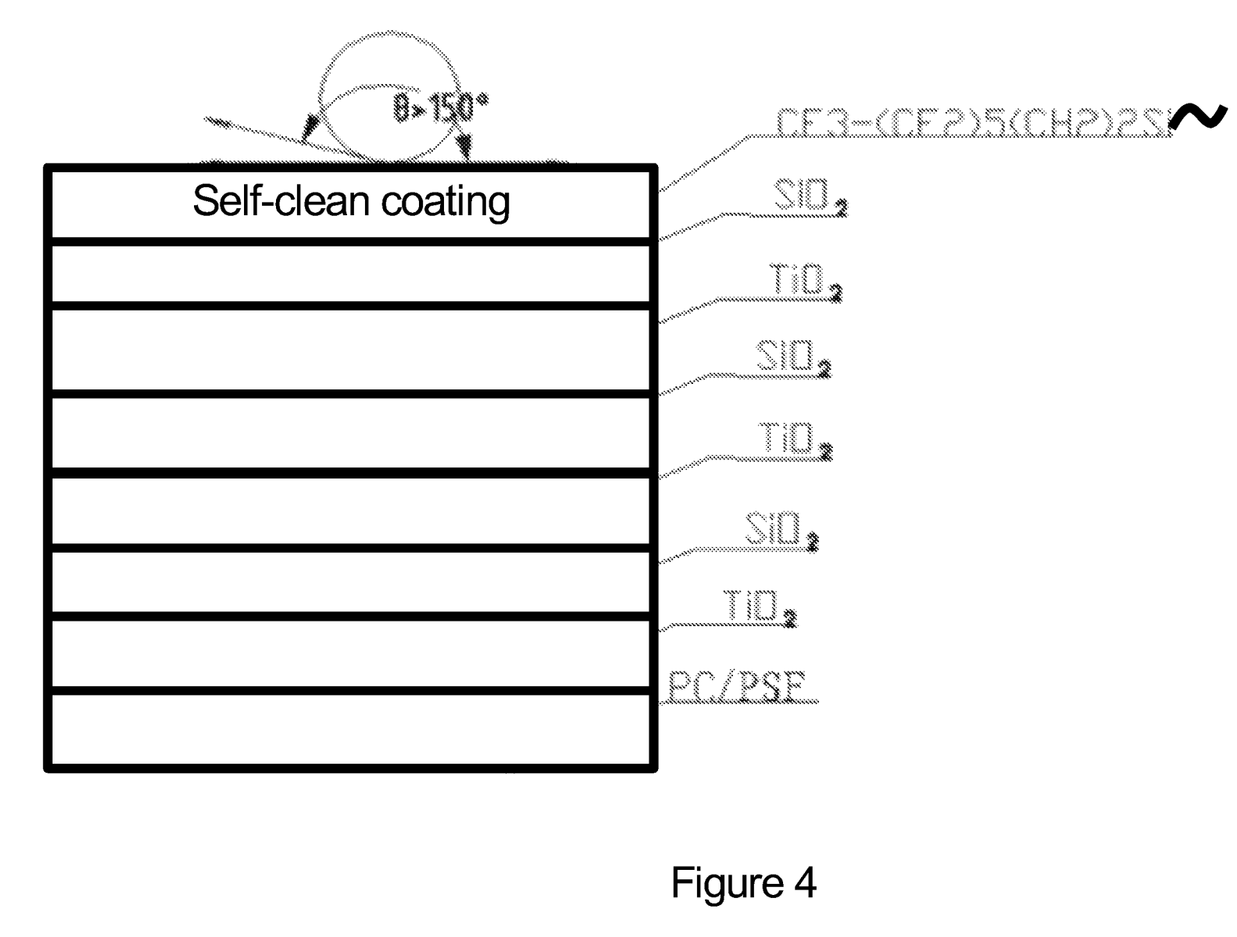
FIG. 4 is a schematic illustration of an exemplary surface modification for a capsule endoscope in accordance with the aspects of the present invention.

A capsule endoscope, having a housing including a front end 11, capsule body 12 and rear end 13, is provided. The front end is transparent. The imaging device is placed inside the housing underneath the surface of front end. The front end 11, capsule body 12 and rear end 13 are all made polycarbonate and have surface modification including a layer of self-clean coating. The exterior surface of the front end 11 is illustrated as FIG. 4. The surface of the front end 11 is sequentially coated with $TiO_2$, $SiO_2$, $TiO_2$, $SiO_2$, $TiO_2$, and $SiO_2$. On top of the last $SiO_2$, a layer of nano scale $CF_3(CF2)_5(CH2)_2Si-$ is grown. The resulted self-clean surface is a low surface energy surface having a contact angle more than 130°. The self-clean surface can effectively prevent residues and mucus accumulated on capsule surface and improve the image quality. The layer of $CF_3(CF2)_5(CH2)_2Si-$ is formed on the capsule surface either in gas phase or in liquid phase. The resulted surface covered by the fluorinated polymer is non-toxic and transparent.

Example 2

A capsule endoscope, having a housing including a front end 11, capsule body 12 and rear end 13, is provided. The front end is transparent. The imaging device is placed inside the housing underneath the surface of front end. The front end 11, capsule body 12 and rear end 13 are all made polycarbonate and only the front end 11 and capsule body have are coated with a layer of self-clean coating. The rear end is not covered by the self-clean coating. The self-clean coating is formed by reacting $CF_3(CF2)_5(CH2)_2SiCl_3$ with a hetero atom of the surface of the housing. This differential surface treatment leads a capsule endoscope, whose rear end having a contact angle smaller than the contact angle of the front end and capsule body. Such capsules can be navigated to a target area having a liquid, to clean the front end thereof by swirling the front end in the liquid or rubbing the front end against the walls of the target area with or without a liquid.

Example 3

A capsule endoscope, having a housing including a front end 11, capsule body 12 and rear end 13, is provided. The housing is made of PSF. The entire housing including front end 11, capsule body 12 and rear end 13 are all coated with optical coatings including $TiO_2$, $SiO_2$, $TiO_2$, $SiO_2$, $TiO_2$, and $SiO_2$. On top of the last $SiO_2$, a layer of nano scale $CF_3(CF2)_5(CH2)_2Si-$ is grown. This surface treatment leads to a capsule endoscope which is not easy to collect any residue or mucous in the digestive track.

Example 4

A capsule endoscope, having a housing including a front end 11, capsule body 12 and rear end 13, is provided. The housing is made of Polycarbonate. The entire housing including front end 11, capsule body 12 and rear end 13 are all coated with optical coatings including $TiO_2$, $SiO_2$, $TiO_2$, $SiO_2$, $TiO_2$, and $SiO_2$. On top of the last $SiO_2$, a layer of nano scale $CF_3(CF2)_5(CH2)_2Si-$ is grown. This surface treatment leads to a capsule endoscope which is not prone to collect any residue or mucous as it travels through the digestive track.

Example 5

A capsule endoscope, having a housing including a front end 11, capsule body 12 and rear end 13, is provided. The housing is made of Polycarbonate. The front end 11 and capsule body 12 are coated with optical coatings including $TiO_2$, $SiO_2$, $TiO_2$, $SiO_2$, $TiO_2$, and $SiO_2$, wherein the last layer of $SiO_2$ forms a nanostructures deposited by photolithography. On top of the nanostructures of $SiO_2$, a layer of nano scale $CF_3(CF2)_5(CH2)_2Si-$ is grown. This differential surface treatment leads to a capsule endoscope whose rear surface has a smaller contact angle than the front surface and body surface thereof. The when the external magnet guides the capsule endoscope into a target area having a liquid, the capsule endoscope can rotate in the liquid or rub against the interior wall of the target area to remove residue or mucus collected on its surface. Or the capsule endoscope can rotate or slightly change its orientation under the influence external magnetic field to make the condensed water droplets roll off from the surface of the capsule.

Example 6

A capsule endoscope, having a housing including a front end 11, capsule body 12 and rear end 13, is provided. The housing is made of Polycarbonate. The front end 11, capsule body 12 and rear end 13 are coated with optical coatings including $TiO_2$, $SiO_2$, $TiO_2$, $SiO_2$, $TiO_2$, and $SiO_2$, wherein the last layer of $SiO_2$ forms a nanostructures deposited by e-beam lithography. FIG. 5 illustrates a surface topography of the layer of $SiO_2$ after the e-beam lithography and FIG. 6 is a cross section diagram thereof. On top of the nanostructures of $SiO_2$, a layer of nano scale $CF_3(CF_2)_5(CH2)_2Si$— is grown. This surface treatment leads to a capsule endoscope which is not prone to collect any residue or mucous as it travels through the digestive track.

Example 7

Growing a layer of fluorinate polymer on the surface of a capsule endoscope.
A capsule endoscope, having a housing including a front end 11, capsule body 12 and rear end 13, is provided. The housing is made of Polycarbonate. The front end 11, capsule body 12 and rear end 13 are cleaned. Then the capsule is placed in an atmosphere which is saturated with $CF_3(CF2)_5(CH2)_2SiCl3$ gas for an extended period of time, then the capsule is exposed to air.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not meant to be exhaustive or to limit the embodiments to the precise forms disclosed. It will be apparent to one of ordinary skill in the art that many modifications and variations are possible in view of the above teachings.

The advantages of the embodiments described are numerous. Different aspects, embodiments or implementations can yield one or more of the following advantages. Many features and advantages of the present embodiments are apparent from the written description and, thus, it is intended by the appended claims to cover all such features and advantages of the invention. Further, since numerous modifications and changes will readily occur to those skilled in the art, the embodiments should not be limited to the exact construction and operation as illustrated and described. Hence, all suitable modifications and equivalents can be resorted to as falling within the scope of the invention.

The invention claimed is:
1. A method to clean a capsule endoscope having a self-clean surface when it is placed in vivo, comprising:
    a) providing a capsule endoscope having a permanent magnetic dipole in situ in a target area having a liquid, wherein the capsule endoscope comprises an illumination device, and imaging device, wherein the illumination device comprises a plurality of LEDs surrounding the image device, both the illumination device and imaging device are placed under a front end of a polymer housing of the capsule endoscope;
    b) changing the position or orientation of the capsule endoscope with respect to the liquid by moving an external magnet;
    c) removing a mucus from the self-clean surface disposed on the front end of the capsule endoscope
    by changing the orientation of the capsule,
    contacting the self-clean surface with the liquid by moving the end of the capsule endoscope having the imaging device above and below the liquid/gas interface,
    while maintaining the capsule endoscope at the same position at a gas/liquid interface; and
    d) examining the interior of the target area by using the imaging device in the capsule endoscope
    wherein the self-clean surface is a surface of the capsule housing,
        does not interfere with a light propagation pathway of the illumination device, placed underneath of the self-clean surface, and
        does not interfere with the light propagation pathway of the imaging device placed underneath of the self-clean surface,
    and
    the self-clean surface is biological safe in the in vivo conditions and formed by essentially with a layer of coating less than 500 nm, providing a contact angle larger than 110 degrees and providing a rolling angle less than 10 degrees and the layer of coating is biological safe in in vivo conditions.
2. The method of claim 1, wherein the cleaning step c) occurs before the examination step d).
3. The method of claim 2, wherein the cleaning step c) further comprising
    suspending the capsule endoscope in a liquid/gas interface in the target area,
    wherein the capsule endoscope and the liquid/gas interface forming a tilt angle.
4. The method of claim 3, wherein the cleaning step c) further comprising
    moving the external magnet up and down to cover and uncover an end of the capsule endoscope having an imaging device by the liquid in the target area.
5. The method of claim 4, wherein the cleaning step c) further comprising
    proving a rotational magnetic field by the external magnet to rotate the capsule endoscope and change its tilt angle from −90 degrees to 90 degrees.
6. The method of claim 4, wherein the surface being cleaned comprises a monolayer of a fluorinated polymer coating.

* * * * *